United States Patent [19]

Lichte

[11] Patent Number: 5,279,601
[45] Date of Patent: Jan. 18, 1994

[54] WATER SEAL WATER MANOMETER

[75] Inventor: Leo J. Lichte, Riverside, Calif.

[73] Assignee: JTL Medical Corporation, Riverside, Calif.

[21] Appl. No.: 791,994

[22] Filed: Nov. 14, 1991

[51] Int. Cl.$^5$ ............................................. A61M 1/00
[52] U.S. Cl. .................................. 604/319; 604/321; 604/327
[58] Field of Search ............. 604/118, 119, 317, 319, 604/321, 327; 137/205

[56] References Cited

U.S. PATENT DOCUMENTS

| | | | |
|---|---|---|---|
| 4,650,477 | 3/1987 | Johnson | 604/321 |
| 4,747,844 | 5/1988 | Elliott | 604/319 |
| 4,955,874 | 9/1990 | Farrar et al. | 604/319 |
| 4,988,342 | 1/1991 | Herweck et al. | 604/321 |
| 5,019,059 | 5/1991 | Goldberg | 604/317 |
| 5,019,060 | 5/1991 | Goosen | 604/319 |

*Primary Examiner*—Randy C. Shay
*Attorney, Agent, or Firm*—Knobbe, Martens, Olson & Bear

[57] ABSTRACT

Disclosed is a vacuum regulator apparatus such as for automatically establishing and maintaining a predetermined vacuum for withdrawing fluid from a chest cavity. The apparatus comprises a water manometer or vacuum regulator portion and a water seal portion. Atmospheric air is vented into the vacuum line through the vacuum regulator portion by displacing a predetermined height column of a fluid such as water. A filter is disclosed for preventing the escape of water from the manometer portion of the apparatus into the downstream vacuum source. A second filter is disclosed for permitting two way gas flow at the upstream end of the manometer portion, but for substantially preventing fluid flow in an upstream direction out of the manometer. Fluid fill ports are disclosed on the manometer and water seal portions for permitting infusion of water to precise and repeatable column heights.

16 Claims, 5 Drawing Sheets

FIG. I

WATER SEAL WATER MANOMETER

FIELD OF THE INVENTION

The present invention relates to a vacuum regulator apparatus and, more particularly, to an apparatus for automatically establishing and maintaining a predetermined vacuum for withdrawing fluid from the chest cavity.

BACKGROUND OF THE INVENTION

A variety of surgical procedures and medical conditions require the use of a carefully regulated fluid vacuum system. For example, draining a patient's chest cavity of accumulated fluid and maintaining a partial vacuum in the patient's chest cavity to permit the lungs to function is sometimes required incident to certain chest surgery procedures. Also, it may be necessary to drain a patient's chest cavity of accumulated fluid and to evacuate the chest cavity incident to accidental puncturing of the chest wall, to ensure that the lungs will function properly.

Several types of prior art drainage systems have been used for this purpose. For example, one type of system uses gravity to effect drainage of the fluids from the chest cavity. In this type of system, a bottle is placed below the level of the patient's chest. The bottle is closed at its top by a rubber stopper through which a first end of a drainage tube is inserted. The second end of the drainage tube is attached to a catheter inserted into the patient's chest.

A sterile liquid such as saline solution is used to fill the bottle to a level which covers the first end of the drainage tube. The sterile liquid is intended to act as a seal or one-way check valve which prevents air from moving back up through the drainage tube to the patient's chest. The bottle is also vented to atmosphere through the rubber stopper so that when the bottle is placed below the level of the patient's chest, gravity will effect drainage of fluid from the pleural cavity into the drainage bottle. Gravity drainage systems, however, tend not to work if the lung is fully collapsed. Moreover, at times there may be a major fluid leak which requires additional drainage capacity.

Another type of drainage system uses a vacuum or suction instead of relying upon gravity. Suction drainage systems typically include a water manometer which is connected to a source of suction and which controls the level of suction applied to the pleural cavity of the patient, because an uncontrolled level of suction may damage the surrounding tissue. The manometer bottle is in turn connected to a bottle which contains a water seal similar to the type of water seal used in a gravity drainage system. The bottle containing the water seal may then be also connected to a third bottle which is used as the drainage bottle for collecting the fluids that are drained from the patient's chest cavity.

One of the disadvantages experienced with the use of this type of three bottle suction drainage system is the rather complicated procedure for setting up the system and interconnecting the three bottles. Also, the system is somewhat inconvenient to use because the bottles must be rinsed, washed and sterilized before they can be used again on other patients.

A more recent system which overcomes some of the disadvantages of the three bottle suction drainage system is illustrated and described in U.S. Pat. Nos. 3,363,626 and 3,363,627. These patents describe a disposable unitary or consolidated "three bottle" apparatus constructed of plastic. Rather than using separate bottles, the apparatus replaces the bottles with separate chambers that are formed as part of a single container. The apparatus retains the basic concept of the three bottle suction drainage system because one of the chambers of the apparatus is used as a manometer, and is connected to a second chamber which is used as a water seal. The second chamber is also connected to a third chamber which is used as the drainage chamber for receiving fluids drained from the patient's chest cavity.

While the apparatus described in these patents simplifies the set up procedure of the basic three bottle suction drainage system and provides for convenient disposal of the system after each use, these apparatus remain relatively complicated in construction and expensive to manufacture and use. Moreover, like the gravity drainage system and the three bottle suction drainage system, these inventions rely upon the use of an underwater seal which is intended to prevent fluids from re-entering the patient's pleural cavity.

In practice, however, an underwater seal does not always prevent fluids from re-entering the patient's chest cavity. For example, if the patient's bronchial tubes are blocked the patient must take deeper breaths in order to expand the lungs to permit air flow around this blockage. When the patient gasps for air or continually takes these kinds of deep breaths, a sufficiently high negative pressure may be developed in the pleural cavity that the liquid used to provide the water seal may be sucked back through the drainage tube and catheter and into the pleural cavity. This obviously increases the risk of contamination to the patient, as well as hampering recovery of the patient's normal respiration. Structure for minimizing the likelihood of backflow is disclosed, for example, in U.S. Pat. No. 4,650,477 to Johnson.

Notwithstanding the foregoing, there remains a need for further improvements to the traditional water seal water manometer system. For example, it can be difficult to fill the water seal bottle of the above designs to precise levels. This is because ascertaining the liquid level in the container during fill or refill is complicated by the fact that such containers are typically positioned at inconvenient locations (e.g., at foot level or under other apparatus) in the patient's room.

Accordingly, it is an object of the present invention to provide a simplified vacuum regulator for use with a chest drainage apparatus which minimizes the risk of reverse flow of liquids from the apparatus into the patient. A further object of the present invention is to provide a vacuum regulator apparatus which can be easily filled with a precise repeatable amount of vacuum regulating liquid. Yet another object of the present invention is to provide a chest drainage apparatus which is easy to use and cost-effective to manufacture.

SUMMARY OF THE INVENTION

There has been provided in accordance with one aspect of the present invention a vacuum regulator, such as for use with a vacuum drainage apparatus for withdrawing excess fluid from a chest cavity. The vacuum regulator comprises a housing, and a downstream vacuum port on the housing adapted for connection to a vacuum source. A vent is provided on the housing in communication with the downstream vacuum port by way of a first air passageway, and an upstream vacuum port is provided on the housing in communication with the downstream vacuum port by way of a second air passageway. When in use, the upstream vacuum port is placed in communication with a reservoir for receiving fluid from the patient.

A vacuum regulating amount of a fluid is disposed within the first air passageway, between the vent and the downstream vacuum port, for providing a predetermined resistance to air flow therethrough. Preferably, at least a portion of the first air passageway extends generally vertically to provide a first chamber for containing a vertical column of the fluid, the vertical height of the fluid determining the degree of resistance to air flow through the first air passageway. A fluid fill port is provided on the housing for providing valved communication with the first air passageway. Preferably, the fluid fill port is disposed at a vertical height on the first chamber corresponding to a desired height of the vertical column of fluid.

Preferably, at least a portion of the second air passageway extends generally vertically to provide a second chamber for containing a vertical column of a second fluid. A second fluid fill port is optimally provided on the housing for providing fluid communication with the column of second fluid. Typically, the first and second fluids are water.

In a preferred embodiment, a barrier is disposed in the first air passageway between the fluid fill port and the downstream vacuum port for permitting downstream air flow through the liquid column and out of the downstream vacuum port but substantially preventing the flow of bubbles or fluid through the barrier. The barrier preferably comprises a mesh filter.

The vent disposed at the upstream end of the first air passageway is preferably provided with a hydrophobic filter for permitting two way gaseous communication but substantially preventing the escape of fluid in an upstream direction, as may otherwise result from back pressure generated by activity in the chest cavity.

In accordance with another aspect of the present invention, there is provided an apparatus for regulating the vacuum in a drainage tube such as used in the chest cavity of a patient, comprising a vacuum regulator chamber and a water seal chamber. The vacuum regulator chamber is provided with an upstream standpipe compartment and a downstream regulator compartment for holding a vacuum regulating amount of a fluid, the upstream standpipe and downstream regulator compartments in fluid communication with each other by way of an end of the standpipe compartment.

The water seal chamber comprises a second upstream standpipe compartment and a downstream water seal compartment. The second upstream standpipe compartment and downstream water seal compartment are in fluid communication with each other by way of an end of the second standpipe compartment.

At least one fluid fill port is provided in communication with the vacuum regulator chamber at a predetermined distance from the end of the standpipe compartment. Preferably, the distance between the end of the standpipe compartment and the fluid fill port corresponds to a column height of fluid selected to produce a predetermined resistance to air flow through the vacuum regulator chamber. Most preferably, the distance is approximately 20 cm.

In accordance with a further aspect of the present invention, there is provided a method of reducing the strength of a vacuum from a vacuum source such as the house vacuum in a hospital, to a desired reduced vacuum level. In accordance with the method, a vacuum regulator is provided as described above. A fluid source is engaged with the fluid fill port on the vacuum regulator portion thereof. Fluid is expressed from the fluid source through the fluid fill port until the level of expressed fluid within the vacuum regulator portion reaches a vertical height above the fluid fill port. Excess fluid above the vertical level of the fluid fill port is withdrawn through the fluid fill port until the fluid level within the vacuum regulator corresponds to the height of the fluid fill port.

The fluid source is thereafter disengaged from the fluid fill port, and the downstream vacuum port is connected to a house vacuum source.

These and further objects and features of the present invention will become apparent from the Detailed Description of Preferred Embodiments which follow, when considered together with the attached claims and drawings.

DETAILED DESCRIPTION OF PREFERRED EMBODIMENTS

Figure 1:
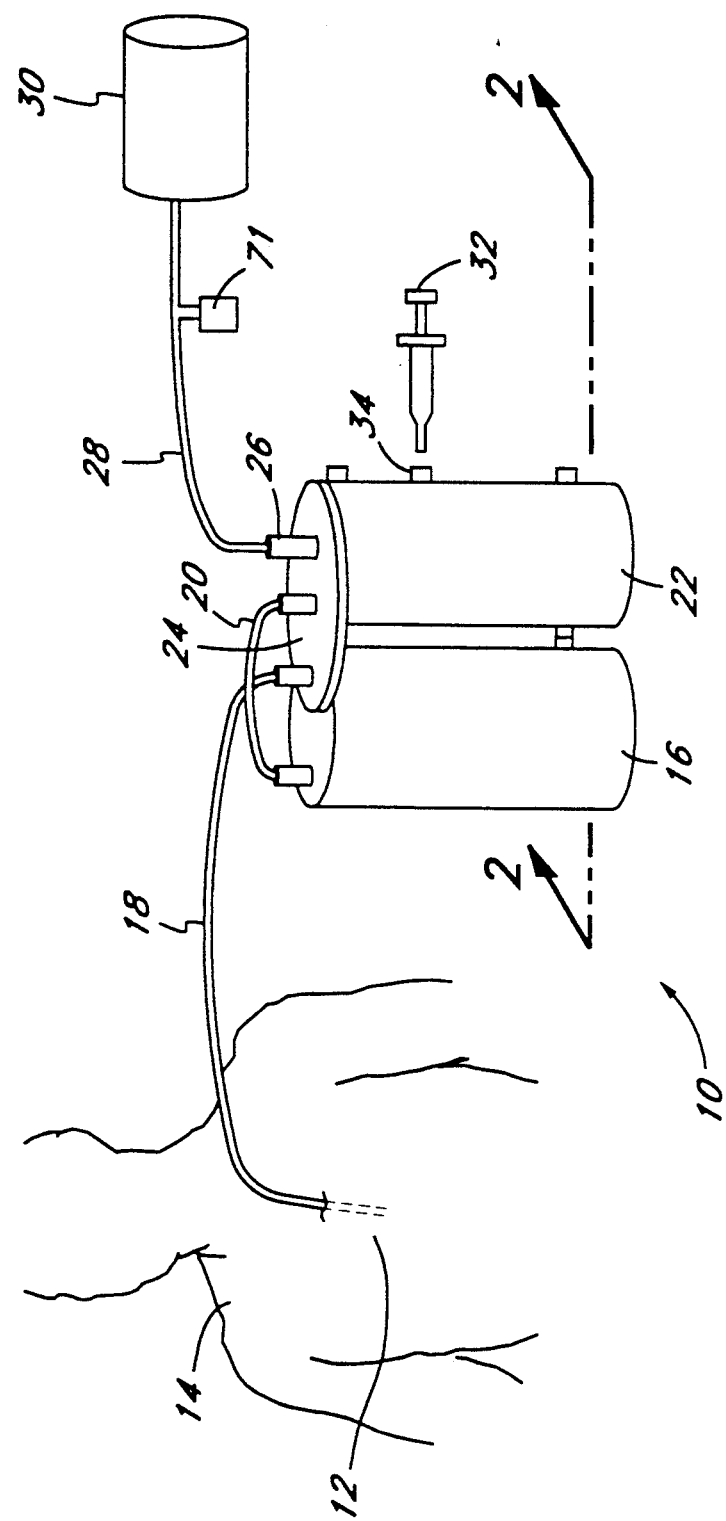
FIG. 1 is a perspective schematic view of one apparatus embodying the present invention.

Referring initially to FIG. 1, an apparatus, generally designated 10, is shown for establishing a predetermined vacuum in the chest cavity 12 of a patient 14. As shown, the apparatus 10 includes a hollow reservoir 16. If desired, the reservoir 16 and other reservoirs disclosed herein can have any of a variety of configurations, as will be apparent to one of skill in the art. A fluid drain line 18 is disposed between the chest cavity 12 and the reservoir 16 to establish fluid communication therebetween.

FIG. 1 also shows that the reservoir 16 is in fluid communication with a container 22 via an air line 20. In one embodiment, the reservoir 16 is physically secured to the container 22 to establish a unitary system. For this purpose, the reservoir 16 and/or container 22 are preferably provided with complementary interlocking structures, such as a bracket 24, which can be secured to the reservoir 16 in a conventional manner.

As shown in FIG. 1, a vacuum fitting 26 is provided on the container 22, and a vacuum line 28 is connected to the vacuum fitting 26. A source 30 of vacuum is attached to the vacuum line 28. Consequently, the source 30 of vacuum is in fluid communication with the interior of the container 22 through the vacuum line 28 and vacuum fitting 26. Source 30 may be a house vacuum, such as is available in many postoperation recovery rooms, or a separate vacuum pump as needed.

Most house vacuum sources are capable of creating relatively high flow rates, sometimes as high as 40 liters per minute. These high flow rates are typically not required in the preferred applications of the present invention. Thus, the water manometer of the present invention may desirably incorporate one of three options for regulating the vacuum source. One, a "variable orifice flow regulator," such as a needle valve, is located in, or in-line with the vacuum inlet port. This variable orifice flow regulator allows the operator of the device to determine and adjust the flow rate that is desired. Alternatively, a "fixed flow regulator," such as a small orifice, is provided in the vacuum inlet port, or in-line with it. The benefit of this approach is that the operator does not have to be concerned about adjusting anything, and the fixed orifice automatically reduces the vacuum source flow rate to a workable level. Third, a combination of the first two options is utilized, whereby a "variable orifice flow regulator" is used in conjunction with a "fixed flow orifice." The benefit here is that the operator has some control over the flow rate, but the fixed orifice limits the upper end of the flow rate such that it prevents extremely high flows from communicating with the manometer. This can also be accomplished by limiting the orifice size opening on the "variable orifice flow regulator."

Additionally, FIG. 1 shows that a syringe 32 can be engaged with a fill fitting 34 to infuse liquid from the syringe 32 into the container 22, as more fully described below.

Figure 2:
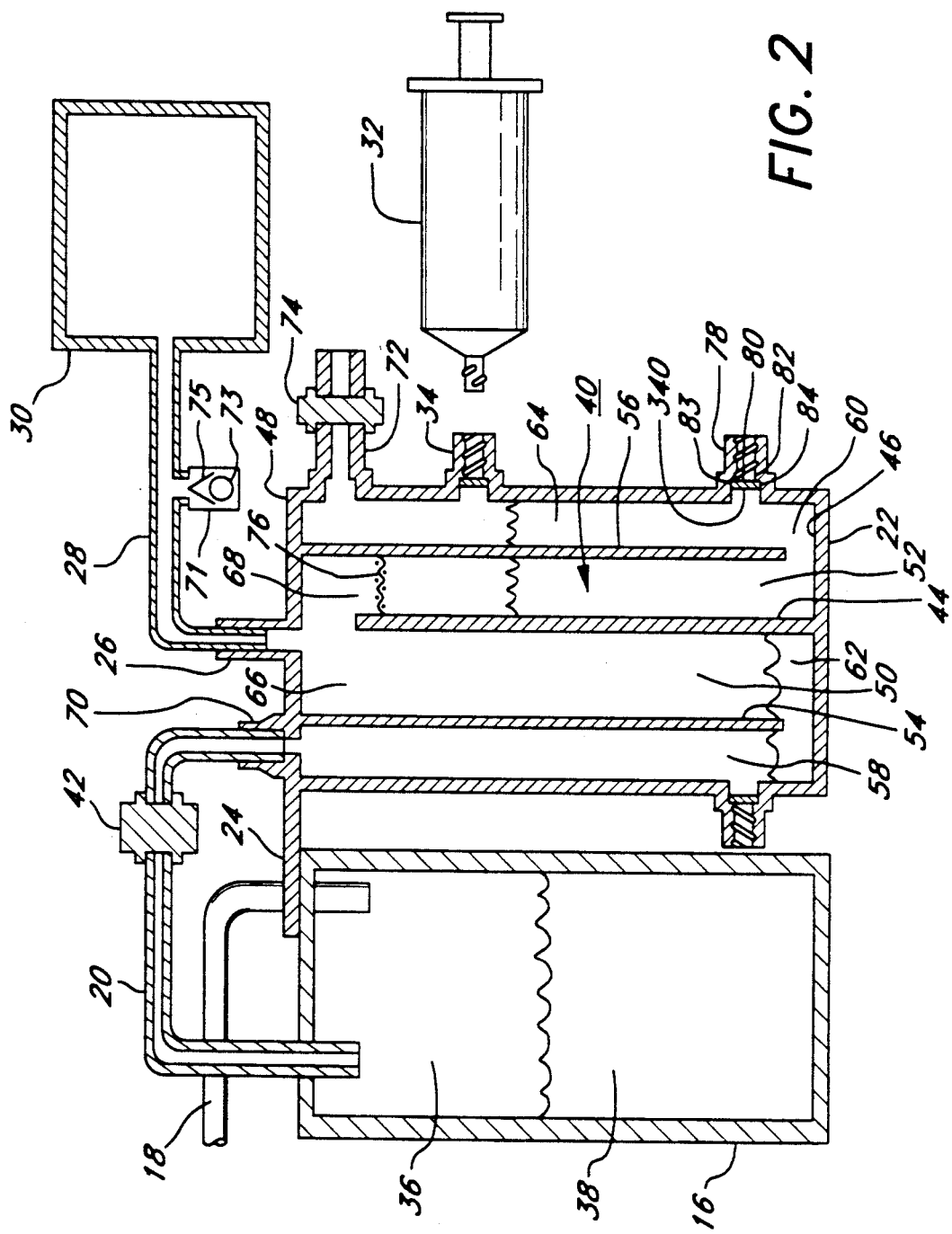
FIG. 2 is an elevational cross-sectional view as seen along the line 2—2 in FIG. 1, with portions shown in phantom.

Now referring to FIG. 2, the details of one embodiment of the apparatus 10 can best be seen. FIG. 2 shows that the reservoir 16 includes an air space 36 that is in communication with the drain line 18. Also, the reservoir 16 includes a space 38 that can hold liquid. It can be appreciated in reference to FIG. 2 that any liquid from the patient 14 which may be communicated to the reservoir 16 through the fluid drain line 18 falls under the force of gravity into the liquid space 38.

Gas in the air space 36 is in communication via the air line 20 to a main vacuum chamber, generally designated 40, which is preferably formed in the container 22. In the preferred embodiment, the air line 20 includes a hydrophobic air line filter 42. By hydrophobic, it is meant that the air line filter 42 permits two-way gas communication between the container 22 and the reservoir 16, but substantially prevents liquid communication between the container 22 and the reservoir 16. Preferably, the filter 42 allows gas to freely pass through it, i.e., the pressure differential across the filter 42 is relatively small.

In one embodiment of the present invention, filters having pore sizes within the range of approximately 0.5 micron to about 10 micron have been found useful. However, different pore sizes may prove advantageous for unique requirements as will be appreciated by one of skill in the art. Suitable materials for the hydrophobic filter 42 include PTFE and polypropylene, available from W. L. Gore and Associates, Inc. and other manufacturers.

It will be appreciated by the skilled artisan that the air line filter 42 thus prevents contamination of the liquid within the reservoir 16, which may be desirably infused back into the patient 14, with liquid from the container 22. This is of particular significance in an application where blood is accumulated in the reservoir 16 for the purpose of reinfusion back into the patient. Moreover, the use of a hydrophobic filter may also be of benefit in the diagnosis of the patient's recovery status. Due to the nature of the filter, air is allowed to move back and forth (bidirectionally) across the filter. This bidirectional air movement acts on the fluid 62 in chambers 50 and 58, causing the fluid of levels to rise and fall in relationship to the slight changes in air pressure. An alternate component, such as a one way or check valve, commonly utilized to prevent flow from the chamber 58 to the reservoir ,16, does not allow for bidirectional flow, thereby preventing the observation of additional diagnostic information.

As discussed above and shown in FIG. 2, the source 30 of vacuum is in communication with the main chamber 40 via the vacuum line 28. If desired, a positive pressure relief valve 71 can be included in the vacuum line 28 to relieve excessive pressure in the main chamber 40 (and, hence, in the reservoir 16 and chest cavity 12 of the patient 14). In the preferred embodiment, the positive pressure relief valve 71 is located in direct communication with the chambers 50 and 52. This is to ensure the least amount of resistance to a pressure deferential in the device.

In one preferred embodiment, the positive pressure relief valve 71 has a ball 73 which abuts a seat 75 when a vacuum is drawn in the vacuum line 28. On the other hand, when a positive pressure exists in the main chamber 40 of about two to three centimeters (2-3 cm) of water, the ball 73 is distanced from the seat 75 to relieve the positive pressure to atmosphere. Any of a variety of check valve constructions can be used as will be apparent to one of skill in the art.

Referring to FIG. 2, a wall 44 extends upwardly from the bottom 46 to near the top 48 of the container 22. As shown, the wall 44 partitions the main chamber 40 into a water seal chamber 50 and a manometer chamber 52. Further, a first barrier 54 extends downwardly from the top 48 of the container 22 into the water seal chamber 50, and the first barrier 54 terminates near the bottom 46 of the container 22. A second barrier 56 extends downwardly from the top 48 of the container 22 into the manometer chamber 52, and the second barrier 56 terminates near the bottom 46 of the container 22. As will be appreciated by one of skill in the art, the first and second barriers 54, 56 can be fashioned in any of a wide variety of ways. Alternatively, separate containers can be used, as long as the basic fluid dynamics described herein are accomplished.

The first barrier 54 establishes a first upstream "standpipe" portion 58 in the water seal chamber 50, and the second barrier 56 establishes a second upstream "standpipe" portion 60 in the manometer chamber 52. Furthermore, each chamber 50, 52 is partially filled to a predetermined level with a liquid. As more fully disclosed below, the water seal chamber is filled with a relatively small amount of liquid such as to a height of preferably about two centimeters (2 cm) above the bottom of barrier 54 and which occludes the passageway around the bottom of barrier 54. In one embodiment, a volume of approximately 6 cc in the water seal chamber 50 is sufficient for this purpose. On the other hand, the manometer chamber 52 is filled with a relatively larger volume of liquid (e.g., 51 cc) up to a height preferably about twenty centimeters (20 cm) above the bottom of barrier 56.

Consequently, each chamber 50, 52 has a respective liquid space 62, 64 and a respective gas space 66, 68. The gas spaces 66, 68 are common, i.e., gas from one space 66, 68 can pass over the wall 44 to the other space 68, 66. The liquid spaces 62, 64 are separated from each other by the wall 44.

The relationship between the volume of the water seal chamber 50 and standpipe compartment 58 can be important in terms of the performance or safety of the device when it is functioning. The water seal chamber 50 is typically filled to a fluid column height of 2 centimeters. The volume of fluid that is required to fill that chamber to a height of 2 centimeters is dependent on the dimensions of that space, as will be readily understood by one of skill in the art. For example, in one embodiment of the device illustrated in FIGS. 3-7, the internal cross sectional dimensions of the water seal chamber 50 are 1 inch (2.54 centimeters) by 0.41 inch (1.04 centimeters) in depth and width. The volume required to fill the level up to 2 centimeters equals 5.3 cc (or milliliters).

Ideally, the total volume of the water seal standpipe compartment 58 is at least about 3 times greater than the volume of fluid that equates to 2 centimeters of vertical height in the water seal chamber 50. In the embodiment described above, the volume of the water seal standpipe compartment 58 is approximately 28 cubic centimeters, which is approximately 5 times greater than the volume in the water seal chamber 50 when filled to a height of 2 centimeters. The reason for this is as follows. In normal operation, air 58 as it evacuates air out of the drainage container. The fluid that is present in compartment 58 is transferred to the "downstream" water seal chamber 50 as the air replaces the fluid and bubbles through it.

In some relatively rare instances, however, it is possible for the vacuum in the drainage container 16 to be greater than the approximately 20 centimeters of vacuum that the device regulates to. When that happens, the differential pressure pushes fluid that is in the water seal chamber 50, back upstream into the compartment 58 and potentially into the drainage container 16. This would cause several problems, one of which is that the fluid in the drainage container (typically blood) is now contaminated.

It is the practice of manufacturers of water seal chambers to install a 'checkvalve' (one-way valve) in the communication line 20 that attaches to the drainage container to prevent backflow of fluids into it. This 'checkvalve' however, sometimes limits the ability of the technician to monitor the patient's breathing patterns and the water seal's function as a diagnostic tool is greatly reduced, as described supra. Thus, one embodiment of the present invention is provided with a bidirectional flow filter 42 upstream of the compartment 58.

Alternatively to, or in addition to the filter 42, backflow of fluid from the compartment 58 into reservoir 16 can be substantially prevented by certain structural modifications such as to the relative volumes of the compartment 58 and chamber 50. By providing a relatively large volume water seal standpipe compartment 58, any fluid that is transferred to it will only reach a height corresponding to the volume of transferred fluid. For example, if the shape and volume of the compartment 58 was the same as that of the water seal chamber 50, the height of the column of water that would be transferred to the compartment 58 would be approximately twice the 2 centimeter that was in each of the chambers in the static condition or 4 centimeters high. If the total space volume in the compartment 58 was 4 times the volume of the 2 centimeter high volume (20+cubic centimeters), than the fluid would not fill the compartment 58, but only half of it. At that point, air that enters the water seal compartment 58 follows behind the water and bubbles through, rather than lifting the water column up and into the drainage container. Although the foregoing discussion incorporates reference numerals from FIGS. 1-2, it is also applicable to the embodiment of FIGS. 3-7 as will be apparent to one of skill in the art.

FIG. 2 also shows that the upstream standpipe compartment 60 is in fluid communication at its upstream end with the atmosphere through a vent 72. As shown, the vent 72 is preferably provided with a means such as a hydrophobic vent filter 74 positioned therein, to substantially prevent liquid in the manometer chamber 52 from splashing out of the vent 72 during pressure surges in the apparatus 10. Filter 74 preferably permits bidirectional gas flow through the vent 72, and is similarly constructed as filter 42, described supra.

A barrier 76 such as a hydrophobic media, fine mesh screen or other baffle or damper structure is preferably positioned in the gas space 68 of the manometer chamber 52. Alternatively, open cell polyurethane foam, or any of a variety of other structures can be used as barrier 76. The purpose of barrier 76 is to break up the bubbles of fluid that materialize when air is drawn into the vent 72, through the upstream compartment 60 and through the fluid in manometer chamber 52. This is preferably accomplished by breaking the surface tension film of the bubble when it hits the barrier.

At certain flows (typically higher flows) these bubbles become large enough to reach the downstream vacuum port 26. When they do, the vacuum flow pulls the bubble out, thereby eventually reducing the amount (height) of the fluid contained in the manometer chamber. This action ultimately affects the performance of the manometer, since the height of the fluid column in the manometer is what regulates the vacuum.

Barrier 76 is preferably coated with a surface tension reducing agent such as a solution of ANTI-FOAM available from Dow Corning Corporation. This ANTI-FOAM breaks up the bubbling effect caused by the air flowing through the liquid. The break up of bubbles decreases the overall height of the liquid, which in turn minimizes the risk of liquid being sucked into the downstream vacuum port. This also allows for an increase in air flow through that chamber, because the height of liquid level increases with flow rate through it.

The pore volume or mesh size of the filter media utilized for barrier 76 can vary depending upon a variety of factors well known to those of skill in the art. For example, too small a pore size undesirably restricts the air flow rate therethrough. On the other hand, a slightly larger pore size will work if the mesh is provided with a coating of anti-foam compared to a mesh without such a coating. Optimum pore sizes can be determined through routine experimentation by one skilled in the art in view of the guidance provided herein. In general, for the preferred application of the invention disclosed herein, pore sizes within the range of from about 1 micron to about 80 microns are presently contemplated.

To permit filling the water seal chamber 50 and manometer chamber 52 with liquid to respective predetermined levels, the present invention contemplates provision of at least one resealable port in the container 22. More particularly, the port 34 mentioned briefly above is formed in the container 22 at a predetermined height above the bottom of barrier 56. Accordingly, the standpipe compartment 60 and, hence, the manometer chamber 52, can be filled with liquid to a preset height through the port 34.

The distance between the fluid level and bottom of barrier 56 will control the strength of the vacuum in air space 36 as will be discussed. In general, the greater the vertical height of the fluid column in chamber 52, the stronger the vacuum up to the limit of the strength of vacuum source 30. Preferably, the port 34 is formed at a distance of about twenty centimeters (20 cm) above the bottom of the second barrier 56 for chest tube drainage applications.

If desired, additional ports 34a which are in all essential respects identical to the port 34 can be formed in the container 22 at other predetermined heights, to provide a selection of predetermined vacuum levels for the user's convenience.

A similar port 34b is preferably formed in the container 22 for establishing a pathway for infusing liquid into the water seal chamber 50 to a predetermined height. Port 34b is in all essential respects identical to port 34, and, in the preferred application of the present invention, is formed in the container 22 at a distance of about two centimeters (2 cm) above the bottom of the first barrier 54.

In describing the ports of the apparatus 10, reference is made to optional port 34a in FIG. 2 as an example. As shown, the port 34a includes a suitable fitting 78 for engaging a source of fluid. As further shown in FIG. 2, the fitting 78 can advantageously be a female luer fitting for engaging a complementary male luer fitting on the syringe 32. Additionally, the port 34a includes a resealable means, e.g., a check valve or pierceable septum, for permitting fluid to be injected into the container 22 and preventing fluid from flowing out of the port 34a when the syringe 32 is disengaged from the port 34a.

In the specific embodiment shown, the check valve includes a seal 80 that is seated within the fitting 78 in the fluid flow path. An annular shoulder 82 is formed on the fitting 78 for receiving seal 80. In accordance with the present invention, seal 80 is biased toward the shoulder 82, so that when the syringe 32 is not engaged with the port 34a, the shoulder 82 engages the seal 80 to provide a fluid seal. When the syringe 32 is properly engaged with the port 34a, the syringe 32 or fluid pressure from the syringe urges the seal 80 away from shoulder 82 to permit liquid in the syringe 32 to be injected into or withdrawn from the container 22. However, any of a wide variety of valves may be utilized which accomplish the same result.

As intended by the present invention, the fluid lines and air lines of the apparatus 10 are made of relatively biologically inert tubular materials which will not readily collapse when evacuated. Accordingly, the fluid lines and air lines can be made of standard plastic intravenous (IV) tubing, stainless steel, etc. Likewise, the container 22 and reservoir 16 are made of suitable biologically inert materials, e.g., clear plastic, glass, etc. Manufacturing of devices embodying the present invention can be accomplished in any of a variety of manners well known in the art, such as by injection molding of a clear thermoplastic material such as polycarbonate.

To prepare for operation of the apparatus 10, the syringe 32 is charged with liquid and then engaged with the port 34. When the syringe 32 is engaged with the port 34, the syringe 32 distances the seal of the check valve that is disposed within the port 34 from the shoulder of the check valve. The plunger of the syringe 32 is advanced into the syringe to inject liquid into the manometer chamber 52. Preferably, the syringe 32 contains sufficient liquid to fill the manometer chamber 52 with liquid to a level above the port 34.

After the liquid has been injected into the manometer chamber 52, the plunger of the syringe 32 is withdrawn to draw liquid from the manometer chamber 52 back into the syringe 32. As the skilled artisan will appreciate, however, only liquid which is above the level of the port 34 is drawn back into the syringe 32. Accordingly, the manometer chamber 52 can be easily filled with liquid to a precise, repeatable level (i.e., the level of the port 34) by infusing all of the liquid in the syringe 32 into the manometer chamber 52 and then withdrawing the plunger of the syringe 32.

After filling the manometer chamber 52, the syringe 32 is disengaged from the port 34, refilled with liquid, and engaged to the port 34b, to similarly fill the water seal chamber 50. This filling process may be repeated during subsequent operation of the apparatus 10 by disengaging the vacuum source 30 and engaging the syringe 32 with one or more of the ports 34, 34a, 34b as appropriate.

When the chambers 50, 52 have been filled, the fluid line 18 is placed into fluid communication with the chest cavity 12 of the patient 14 as is well known, and the vacuum source 30 is energized. This establishes a vacuum in the vacuum line 28 and gas spaces 66, 68. When the vacuum exceeds about 2 cm of water, i.e., a sufficient negative pressure to overcome the weight of the liquid column in the standpipe portion 58 of the water seal chamber 50, the vacuum is consequently established in the air line 20 and air space 36 of the reservoir 16 and, hence, in the chest cavity 12 of the patient 14.

The pressure within the apparatus 10 continues to decrease as the vacuum source 30 evacuates the interior chambers 50, 52, and air space 36 of the apparatus 10 and the chest cavity 12 of the patient 14. The pressure continues to decrease until one of two events occurs. First, the pressure will decrease until the source 30 of vacuum can no longer lower pressure in the system. In other words, the pressure in the apparatus 10 and chest cavity 12 cannot decrease beyond the capacity of the vacuum source 30 to evacuate the interior of the space defined by the chest cavity 12 and apparatus 10.

Second, when the vacuum (i.e., negative pressure) in the gas space 68 exceeds the predetermined maximum vacuum as set by the height of the water column in the manometer chamber 52, the vacuum will be sufficient to cause air from the atmosphere to enter the vent 72 and manometer chamber 52. Incoming air displaces fluid in the upstream compartment 60 by forcing it down and around the end of barrier 56 so that the air bubbles up into gas space 68. This air drawn into the gas space 68 thereby limits the vacuum within the space 68 (and, hence, the chest cavity 12 of the patient 14) to that corresponding to the height of the liquid within the manometer chamber 52.

As water is displaced from compartment 60 into manometer chamber 52, the water level in chamber 52 is elevated. Preferably, as discussed in detail in connection with FIGS. 3-7, chambers 60 and 52 are relatively dimensioned so that the elevation of the water level in chamber 52 will not be sufficient to cause water to spill into the water seal side of the device or enter the vacuum source.

The operating manometer device thus has a regulated vacuum (negative pressure) in chamber 68 and all areas in direct communication therewith of about −20 cm H₂O. In the event that pressure within the chest cavity 12 and chamber 68 for some reason changes from negative to positive, (above atmospheric pressure), such as can occur when the patient 14 is experiencing certain breathing difficulties, air should be vented to the atmosphere to relieve the positive pressure. For this purpose, positive pressure relief valve 71 is provided as has been discussed. Optimally, positive pressure is never permitted to exist in the chamber 68 and points in communication therewith. Practically, however, most positive pressure relief valves have a threshold break pressure, and preferably the valve will maintain any positive pressure to more than about 2-3 cm H₂O.

Accordingly, the skilled artisan will appreciate that the apparatus 10 can easily and precisely establish a predetermined vacuum in the chest cavity of a patient, despite variations in the vacuum source. Also, the apparatus 10 can establish a predetermined maximum vacuum that can be drawn in the chest cavity of a patient. Further, the apparatus 10 establishes a predetermined maximum positive pressure that can exist within the chest cavity of a patient.

FIGS. 3-7 show a preferred embodiment of the vacuum regulator of the present invention, generally designated 100. As shown, the vacuum regulator container 100 is substantially functionally similar to the container 22 shown in FIGS. 1 and 2 and described above.

The vacuum regulator container 100 generally comprises a housing having a front wall, side walls and a top and bottom which are conveniently integrally molded as a single unit. In addition, partitions are preferably provided within the housing for separating the various chambers, as will be described. The partitions may also be integrally molded within the housing, or may be secured therein as a separate manufacturing step such as by adhesives, solvent or thermal bonding techniques known in the art. A back wall 132 completes the housing by sealing the various side walls and partitions to produce a plurality of discrete internal chambers. Back wall 132 may be provided with any of a variety of structures such as flanges or grooves for sealingly engaging the side walls and interior partitions.

A partition 101 extends from the top 108 of the container 100 to the bottom 110 of the container 100 to establish a water seal chamber 102 and a manometer or vacuum regulator chamber 104. As shown, the partition 101 is mounted between two flanges 103, 105 (FIGS. 3-5) which are formed on an interior surface of the back wall 132 of container 100, and the partition 101 can be attached to the flanges 103, 105 by solvent or thermal bonding. When the container 100 is made of plastic, the partition 101 can also be attached to the flanges 103, 105 by sonic welding or rf sealing. Alternatively, the partition 101 can be formed integrally with the front, side and rear walls of container 100 such as in an extrusion molding process.

A barrier 106 (see FIG. 6) extends from the top 108 of the water seal side of the container 100 to near the bottom 110 of the container 100 to establish an upstream water seal compartment 112. Thus, the relatively downstream water seal chamber 102 is in fluid communication with the upstream water seal compartment 112 via a passage between the bottom of barrier 106 and the bottom 110 of the container 100. Fluid communication can also be accomplished through one or more ports in the barrier 106 as will be readily understood. As shown, the barrier 106 is mounted between two flanges 114, 116, (FIGS. 3-5) which are formed on an interior surface of the rear wall of the container 100.

The upstream water seal compartment 112 is provided with a port 118 (FIGS. 3 and 4) which can be connected to a connecting line (not shown) similar to the air line 20 shown in FIGS. 1 and 2, to establish fluid communication between the container 100 and a reservoir (not shown) functionally similar to the reservoir 16. The rear wall 132 is preferably provided on its exterior surface with a mounting bracket (not shown) for mounting the device adjacent or directly to a reservoir for receiving fluid from the patient.

FIGS. 3-7 show that an upstream manometer standpipe or compartment 120 is formed on the vacuum regulator side of the partition 101. As shown, the upstream standpipe 120 is in fluid communication with the downstream vacuum regulator chamber 104 via an orifice 122 near the bottom 110 of the container 100. A vent 124 at the upstream limit of standpipe 120 establishes a pathway for communication between the standpipe 120 and atmosphere.

It is to be appreciated in reference to FIGS. 3-7 that the manometer standpipe compartment 120 is a relatively low volume container. Stated differently, while the standpipe 120 can hold a relatively high vertical column of water, the transverse cross-sectional area of the standpipe 120 is relatively small. Consequently, the volume of water which can be held in the standpipe 120 is small, compared to the volume of the manometer chamber 104. Thus, when the vacuum source draws air down standpipe 120 and into chamber 104, the volume of water displaced from standpipe 120 and into chamber 104 will not raise the water level in chamber 104 high enough to escape into the vacuum source. Preferably, a mesh screen or other structure is positioned between the fluid level in chamber 104 and the fitting 126 as has been discussed.

Figure 3:
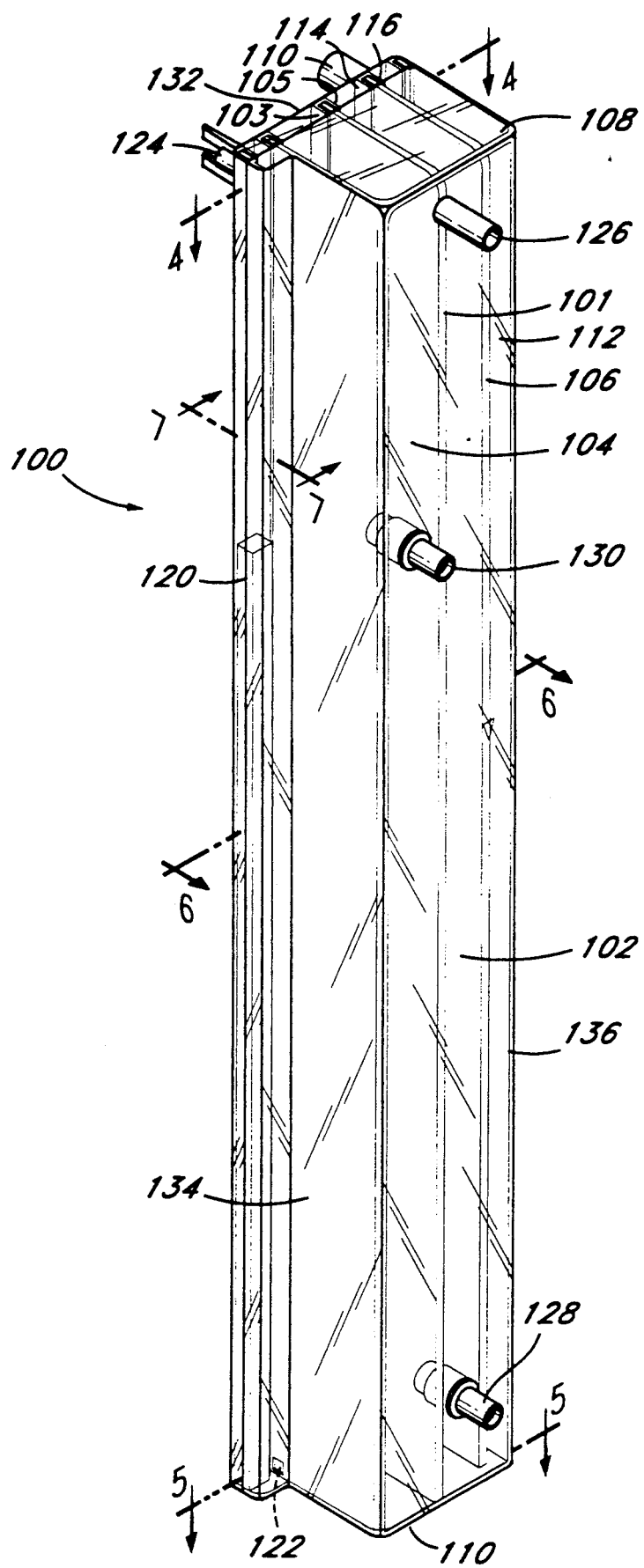
FIG. 3 is a perspective view of another, preferred embodiment of the present invention.
Figure 4:
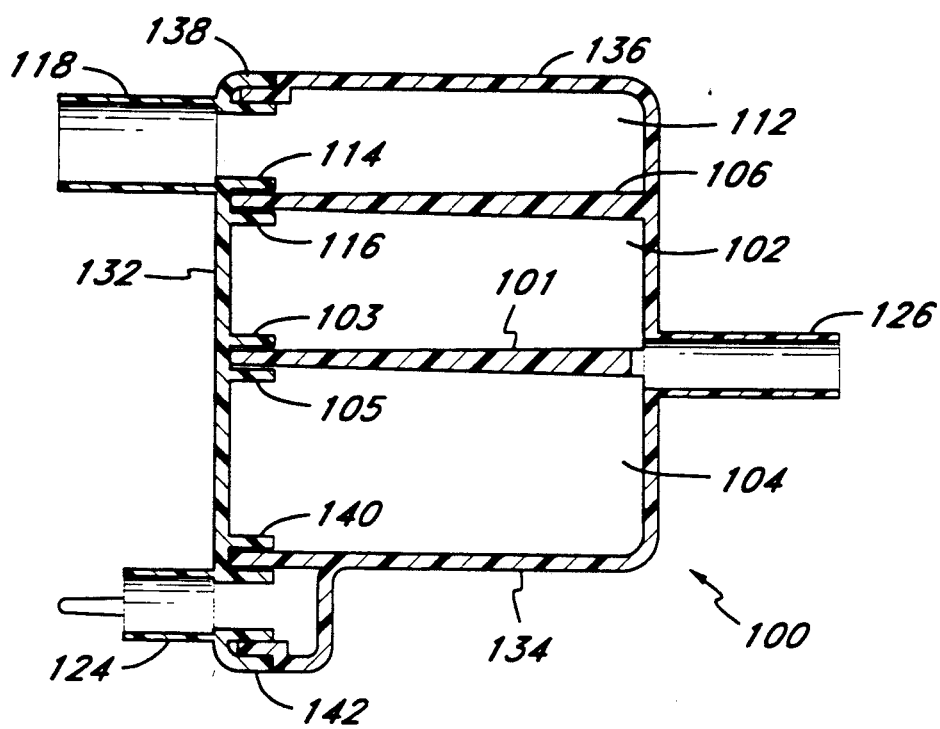
FIG. 4 is a cross-sectional view of the embodiment shown in FIG. 3, as seen along the line 4—4 in FIG. 3.

As best shown in FIGS. 3 and 4, a port, preferably provided with vacuum fitting 126, is formed on the container 100. Fitting 126 can be connected to a source of vacuum (not shown) to establish a pathway for communication between the source of vacuum and both the manometer chamber 104 and the water seal chamber 102 (see FIG. 4).

The container 100 is also formed with ports 128, 130 for respectively filling the water seal chamber 102 and manometer chamber 104. The ports 128, 130 can be constructed substantially identically to port 34 shown in FIG. 2. Alternatively, each of the ports 128, 130 can have a valve element (not shown) disposed therein which is materially biased into a configuration wherein fluid flow out of the particular port 128, 130 is controlled. The valve element can be displaced when a syringe (not shown) is urged inwardly against the valve element to thereby permit fluid communication through the port 128, 130. An example of such a valve element is the luer style syringe check valve marketed by Halkey Medical Division of Halkey-Roberts.

Figure 5:
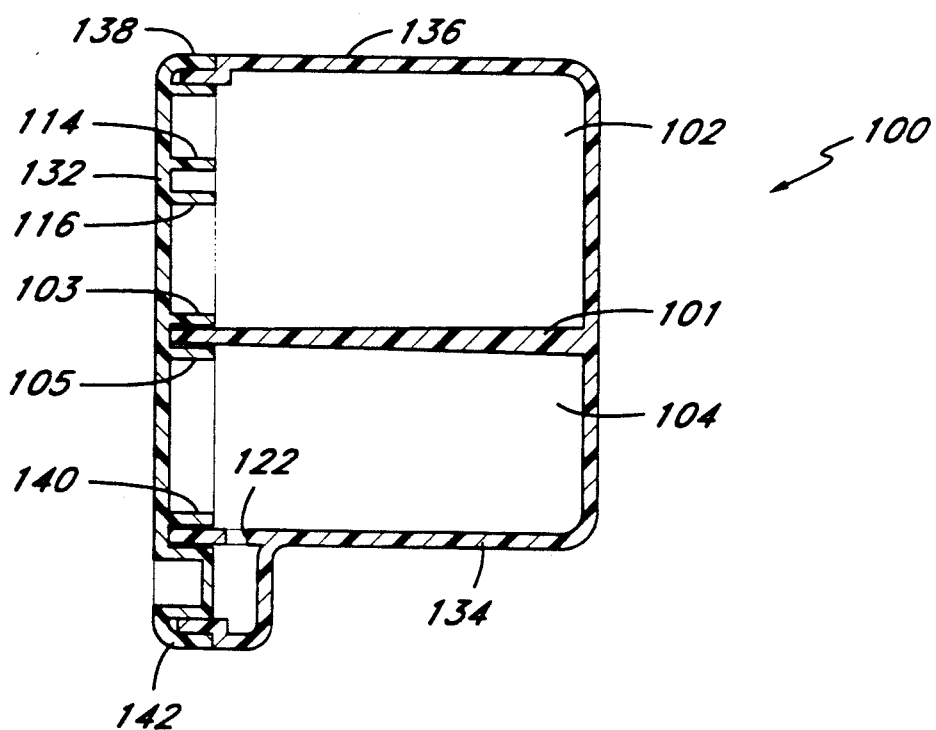
FIG. 5 is a cross-sectional view of the embodiment shown in FIG. 3, as seen along the line 5—5 in FIG. 3.
Figure 6:
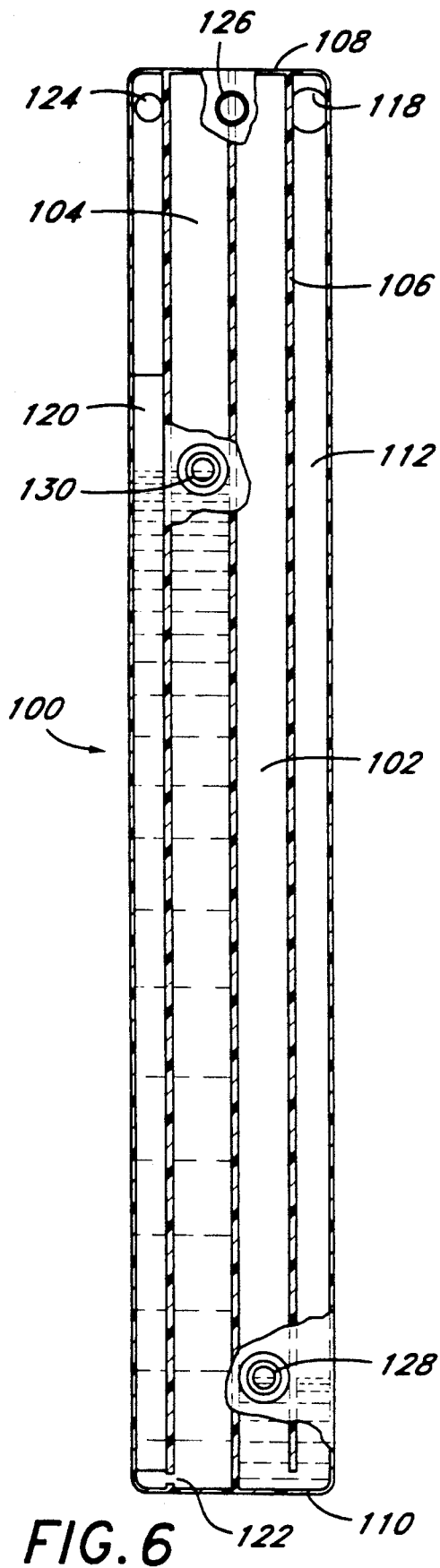
FIG. 6 is a cross-sectional view of the embodiment shown in FIG. 3, as seen along the line 6—6 in FIG. 3.
Figure 7:
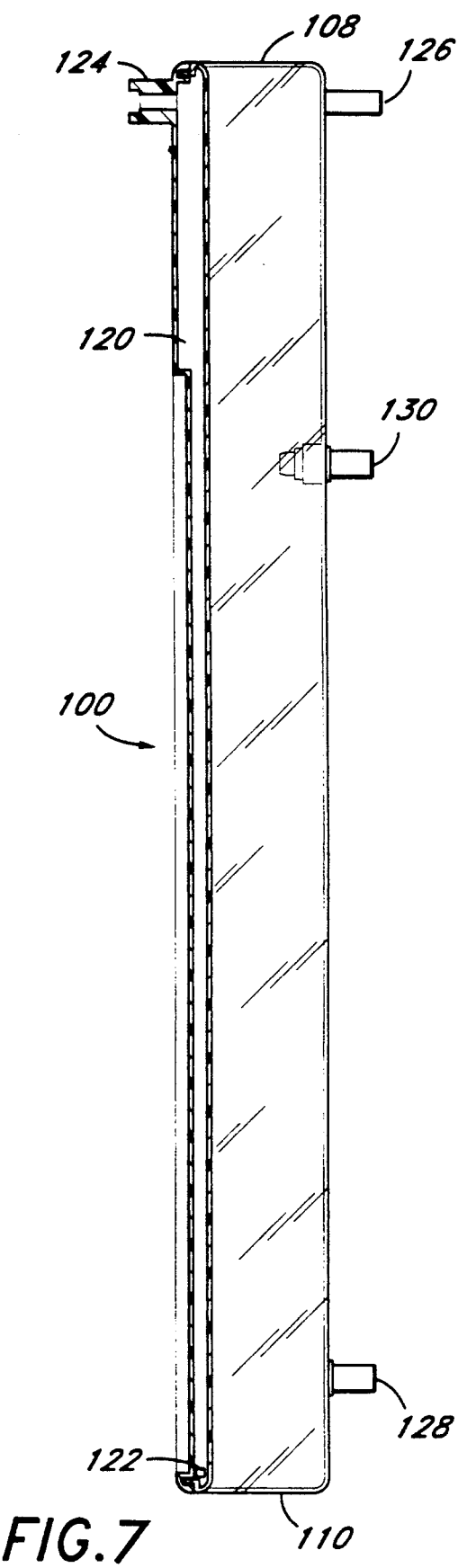
FIG. 7 is an elevational cross-sectional view of the embodiment shown in FIG. 3, as seen along the line 7—7 in FIG. 3.

Construction of the present embodiment can be conveniently accomplished by injection molding the front and sidewalls of the container 100, together with partition 101 and barrier 106 as an integral unit. Back wall 132 may be separately molded and then secured thereto using conventional means. FIGS. 4 and 5 also show that the back 132 of the container 100 can be attached to the sides 134, 136 of the container 100 by flanged fixtures 138, 140, and 142, in addition to the attachments provided by the flanges 103, 105, 114, 116 described previously. It is to be understood that the back 132 can alternatively be formed integrally with the sides 134, 136 of the container 100. In its operation, the container 100 functions essentially the same as the container 22, described previously.

While the specific embodiments disclosed in detail herein are fully capable of achieving the objects hereinbefore stated, it is to be understood that the scope of the present invention is only to be limited by reference to the appended claims.

I claim:

1. An apparatus for regulating the vacuum in a drainage tube such as used in the chest cavity of a patient, comprising:
   a vacuum regulator chamber having a first upstream standpipe compartment and a downstream regulator compartment for holding a vacuum regulating amount of a fluid, said upstream standpipe and downstream regulator compartments being in fluid communication with each other by way of a first end of said first standpipe compartment;
   a water seal chamber having a second upstream standpipe compartment and a downstream water seal compartment, said second upstream standpipe compartment and downstream water seal compartment being in fluid communication with each other by way of a first end of said second standpipe compartment, said first upstream standpipe compartment of said vacuum regulator being in communication with said downstream water seal compartment; and
   a fluid fill port in communication with the vacuum regulator chamber at a predetermined distance from the end of said first standpipe compartment;
   wherein said distance corresponds to a column height of fluid selected to produce a predetermined resistance to air flow through said vacuum regulator chamber.

2. An apparatus as in claim 1, wherein the fluid fill port is disposed approximately 20 cm above the end of the standpipe compartment.

3. An apparatus as in claim 1, further comprising a second fluid fill port in communication with the water seal chamber.

4. An apparatus as in claim 3, wherein said second fluid fill port is disposed vertically above the first end of the second standpipe compartment.

5. An apparatus as in claim 1, wherein the fluid fill port comprises a valve for permitting the selective introduction and withdrawal of fluid therethrough.

6. An apparatus as in claim 1, wherein the fluid fill port is in direct communication with the downstream regulator compartment.

7. An apparatus as in claim 1, further comprising a downstream vacuum port in communication with both the downstream regulator compartment and the downstream water seal compartment.

8. A vacuum regulator, comprising:
   a housing;
   a downstream vacuum port on the housing, adapted for connection to a vacuum source;
   a vent on the housing in communication with the downstream vacuum port by way of a first air passageway;
   an upstream vacuum port on the housing in communication with the downstream vacuum port by way of a second air passageway.
   a vacuum regulating amount of a first fluid disposed within the first air passageway, between the vent and the downstream vacuum port, for regulating the air flow therethrough; and
   a first fluid fill valve on the housing for providing communication with the first air passageway;
   wherein at least a portion of the first air passageway extends generally vertically to provide a first chamber for containing a vertical column of said first fluid, the vertical height of the first fluid regulating the air flow through the first air passageway, and said first fluid fill valve is disposed at a vertical height on said first chamber corresponding to a predetermined height of the vertical column of said first fluid.

9. A vacuum regulator as in claim 8, wherein at least a port of the second air passageway extends generally vertically to provide a second chamber for containing a vertical column of a second fluid, and further comprising a second fluid fill valve on the housing for providing fluid communication with said vertical column of said second fluid.

10. A vacuum regulator as in claim 9, further comprising a hydrophobic filter upstream of the first air passageway.

11. A vacuum regulator as in claim 8, further comprising a barrier means disposed in the first air passageway between the first fluid fill valve and the downstream vacuum port, said barrier means for permitting air flow through the vertical column of said first fluid and out of the downstream vacuum port but substantially preventing the flow of bubbles or fluid through the barrier means.

12. A vacuum regulator as in claim 11, wherein said barrier comprises a mesh filter.

13. A vacuum regulator as in claim 12, wherein said mesh has a pore size within the range of from about 1 micron to about 80 microns.

14. A vacuum regulator as in claim 8, wherein said first chamber in said first air passageway further comprises a divider extending generally vertically downwardly therein to define an upstream compartment in direct communication with the vent, and a downstream compartment in direct communication with the downstream vacuum port, and wherein the upstream and downstream compartments are in fluid communication with each other around the end of said divider.

15. A vacuum regulator as in claim 14, wherein the first fluid fill valve is in fluid communication with the downstream compartment.

16. A vacuum regulator as in claim 14, wherein the first fluid fill valve is disposed on the housing at a height of approximately 20 cm above the lower edge of the divider.

* * * * *